United States Patent [19]
Goodby et al.

[11] Patent Number: 5,750,050
[45] Date of Patent: May 12, 1998

[54] DISCOTIC COMPOUNDS FOR USE IN LIQUID CRYSTAL MIXTURES

[75] Inventors: John William Goodby; Michael Hird; David Richard Beattie; Paul Hindmarsh, all of Hull; George William Gray, Dorset; Damien Gerard McDonnell, Malvern; John Clifford Jones, Malvern; Timothy Jonathan Phillips, Malvern, all of United Kingdom

[73] Assignee: Secretary of State for Defence in her Britannic Majesty's Government of the U.K. of Gt. Britain and N. Ireland of Defence Evaluation Research Agency, DRA, United Kingdom

[21] Appl. No.: 564,211
[22] PCT Filed: Jun. 16, 1993
[86] PCT No.: PCT/GB93/01291
  § 371 Date: Feb. 28, 1996
  § 102(e) Date: Feb. 28, 1996
[87] PCT Pub. No.: WO94/29263
  PCT Pub. Date: Dec. 22, 1994
[51] Int. Cl.$^6$ ............ C09K 19/32; C09K 19/52; C07C 69/76
[52] U.S. Cl. ............ 252/299.62; 560/56; 560/64; 560/80; 428/1
[58] Field of Search ............ 252/299.62, 299.01; 560/56, 64, 80; 428/1

[56] References Cited

U.S. PATENT DOCUMENTS

| | | | |
|---|---|---|---|
| 4,333,709 | 6/1982 | Dubor's et al. | 252/299.62 |
| 5,518,783 | 5/1996 | Kanata et al. | 428/1 |

OTHER PUBLICATIONS

Phillips et al., "On the Influence of Short Range Order Upon the Physical Properties of Triphenglene Nematic Discogens", Liq. Cryst. vol. 15 No. 2. pp. 203–215, 1993.

(List continued on next page.)

*Primary Examiner*—Shean C. Wu
*Attorney, Agent, or Firm*—Nixon & Vanderhye

[57] ABSTRACT

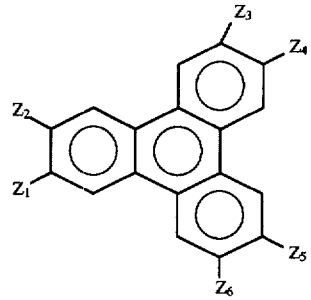

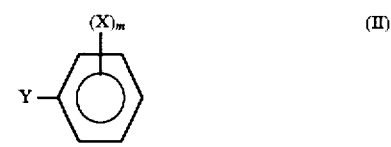

Liquid crystal compounds have been synthesized of general formula (I) and may be mixed with other liquid crystal compounds to give useful liquid crystal mixtures which may then be used in liquid crystal devices. Such devices include linear and non-linear electrical, optical and electro-optical devices, magneto-optical devices and devices providing responses to stimuli such as temperature changes and total or partial pressure changes. Formula (I) where each $Z_{1-6}$ is given by formula (II), where Y for each of $Z_{1-6}$ is independently COO, OCO, $CH_2O$ and $OCH_2$, m defines the number of substituents on each of $Z_{1-6}$ and is independently 0–5,and X is independently for each substituent on each of $Z_{1-6}$ alkyl (straight chain, branched and chiral), alkoxy (straight chain, branched or chiral), alkanoyl (straight chain, branched or chiral), alkenyl (straight chain, branched or chiral), halogen, halogenoalkyl (straight chain, branched or chiral) and CN, provided that at least one of $Z_{1-6}$ has at least one substituent X, and excluding where m is 1 for each of $Z_{1-6}$, Y is COO for each of $Z_{1-6}$ and X is n-alkyl or n-alkoxy positioned para to Y for each of $Z_{1-6}$ and also where M is 5 for each of $Z_{1-6}$, Y is COO for each of $Z_{1-6}$ and for each $Z_{1-6}$ X is selected as n-alkoxy positioned para to Y and fluoride for all other substituents.

10 Claims, 10 Drawing Sheets

OTHER PUBLICATIONS

Voucher et al., Orientation of Discotic Mesophase's, Mol. Cryst. and Liq. Cryst. vol. 66. No. 1-4, pp. 103-114, 1981.

Chapuget et al., "Trimerization of Aromatic Orthediasters: New Development.", Tetrahedron, vol. 47, No. 4/5, pp. 791-798, 1991.
CA 95: 52991, 1981.
CA 100: 93661, 1984.

DISCOTIC COMPOUNDS FOR USE IN LIQUID CRYSTAL MIXTURES

This is a national phase filing of PCT/GB93/01291 having an international filing date of Jun. 16, 1993, published as WO94/29263 Dec. 22, 1994.

BACKGROUND OF THE INVENTION

This invention relates to discotic compounds and to their use in liquid crystalline materials and liquid crystal devices.

The majority of known liquid crystalline compounds have a generally rod-shaped molecular structure, and are often characterised by nematic and/or smectic mesophases. However, there are a number of known compounds which are characterised by a generally disc-like molecular structure. These compounds are termed discotic compounds, which can be characterised by anisotropic mesophase(s).

Discotic compounds can be based on a number of "cores", eg benzene, truxene, metallophthalocyanine and triphenylene described in S Chandrasekhar and G S Ranganath in Rep Prog Phys 53 (1990) pp 57–84. Nguyen Huu Tinh et al (Mol. Cryst. Liq. Cryst., (1981), Vol 68, pp 101–111) describe 2,3, 6,7, 10,11 triphenylene n-alkoxy (and n-alkyl) esters. C Vauchier et al (Mol. Cryst. Liq Cryst., Vol 66 (1981) pp 103–114) have also described 2,3, 6,7, 10,11 n-alkoxy benzoates and n-alkoxy tetra-fluoro substituted benzoates of triphenylene.

DETAILED DESCRIPTION OF THE INVENTION

Figure 1:
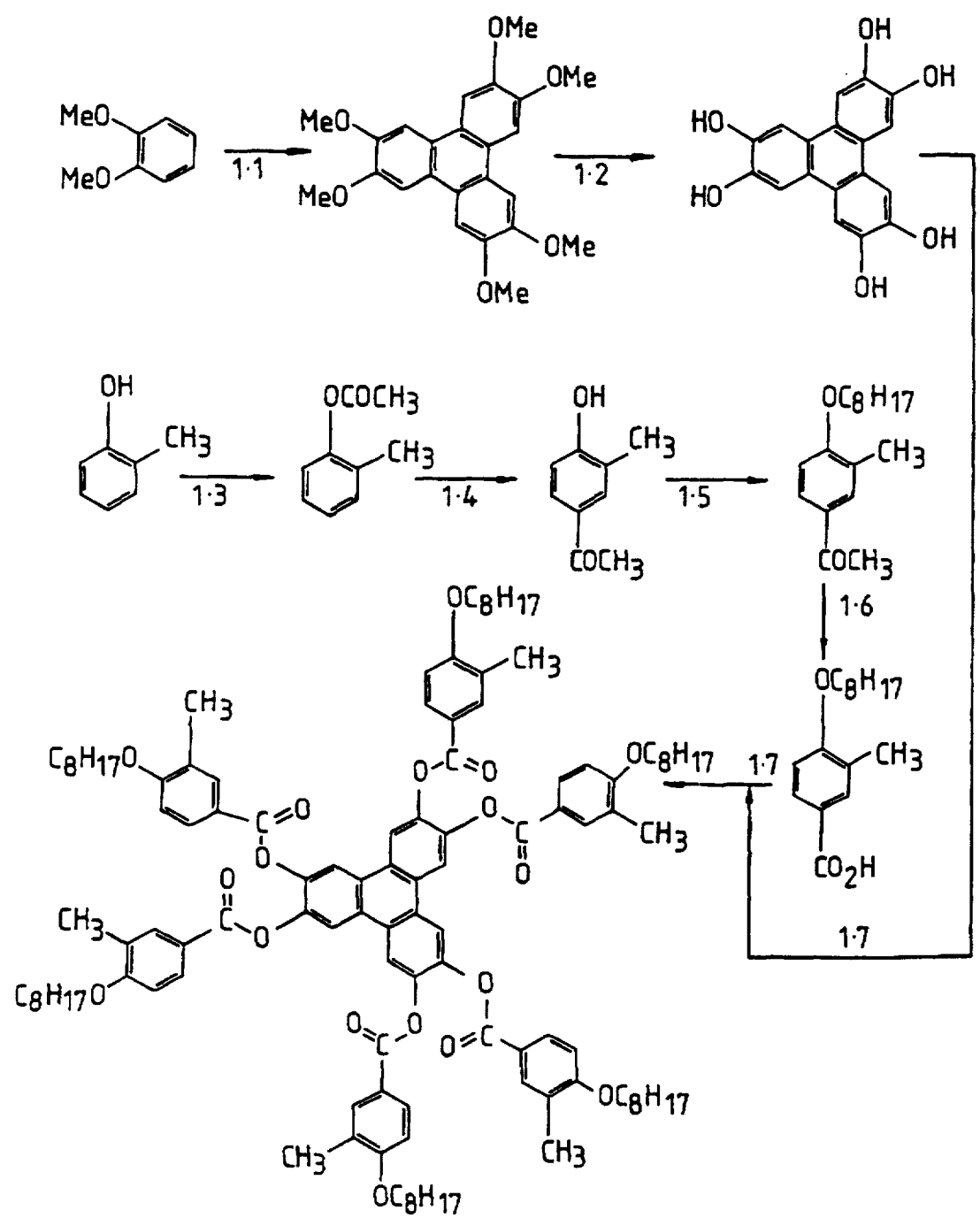
FIG. 1 is a synthetic route for preparing the compound of Example 1.
Figure 2:
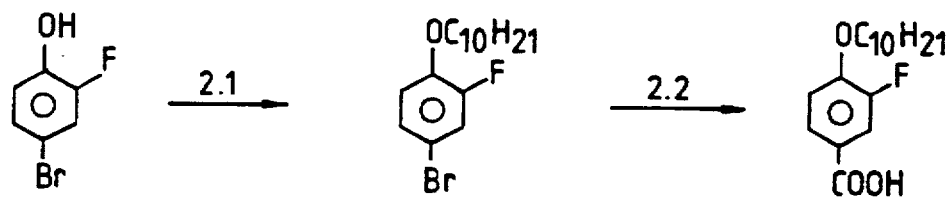
FIG. 2 is a synthetic route for preparing the compound of Example 2.
Figure 2:
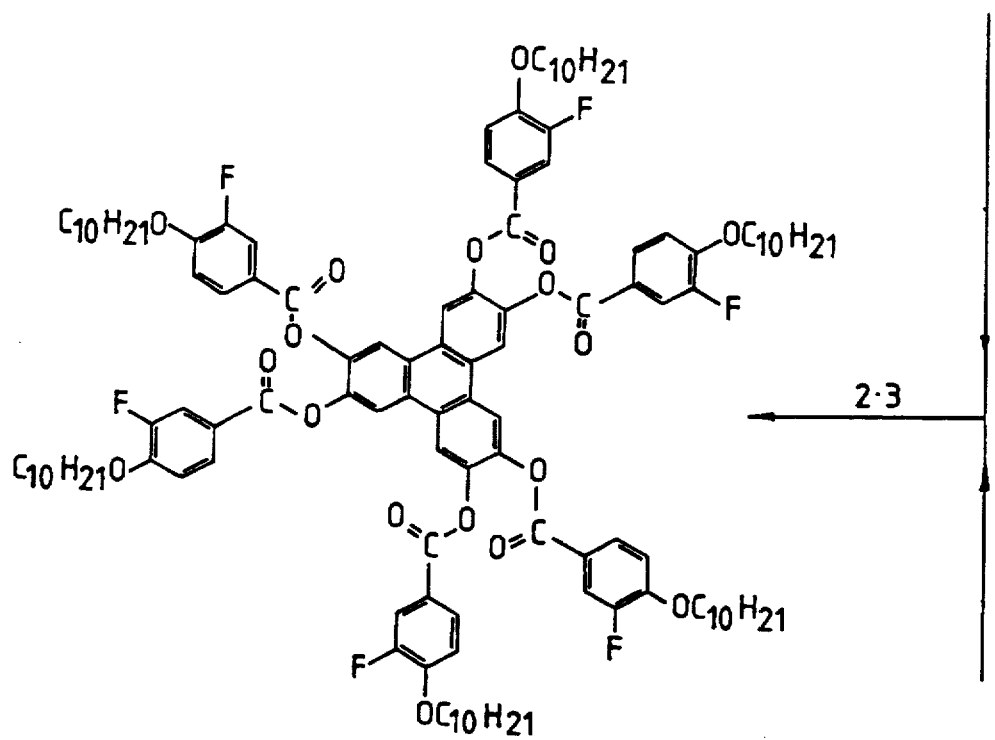
Figure 2:
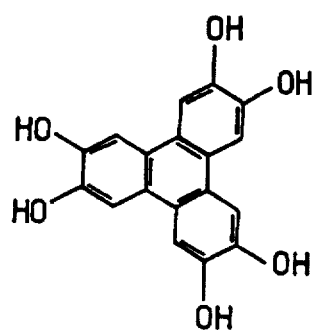
Figure 3:
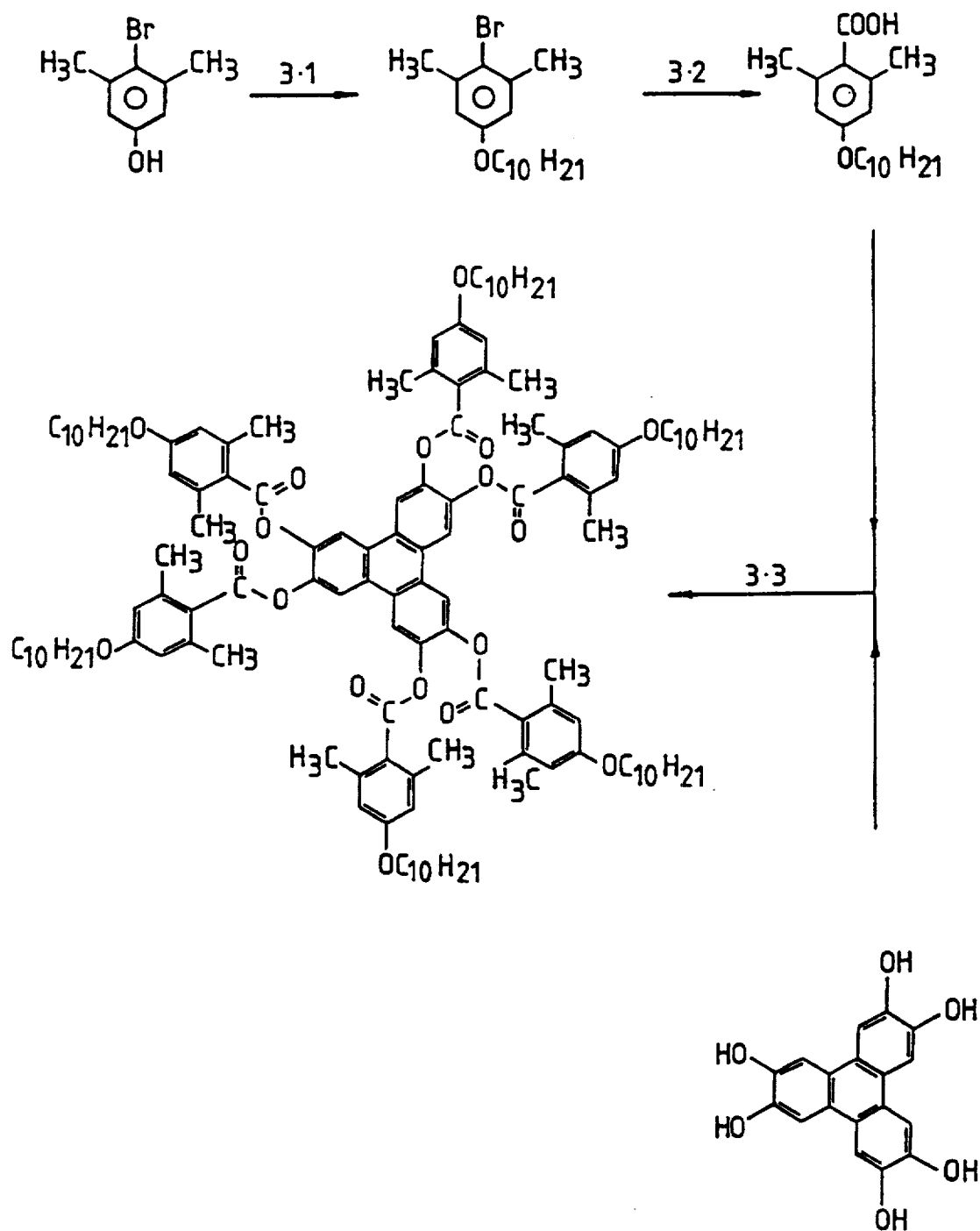
FIG. 3 is a synthetic route for preparing the compound of Example 3.
Figure 4:
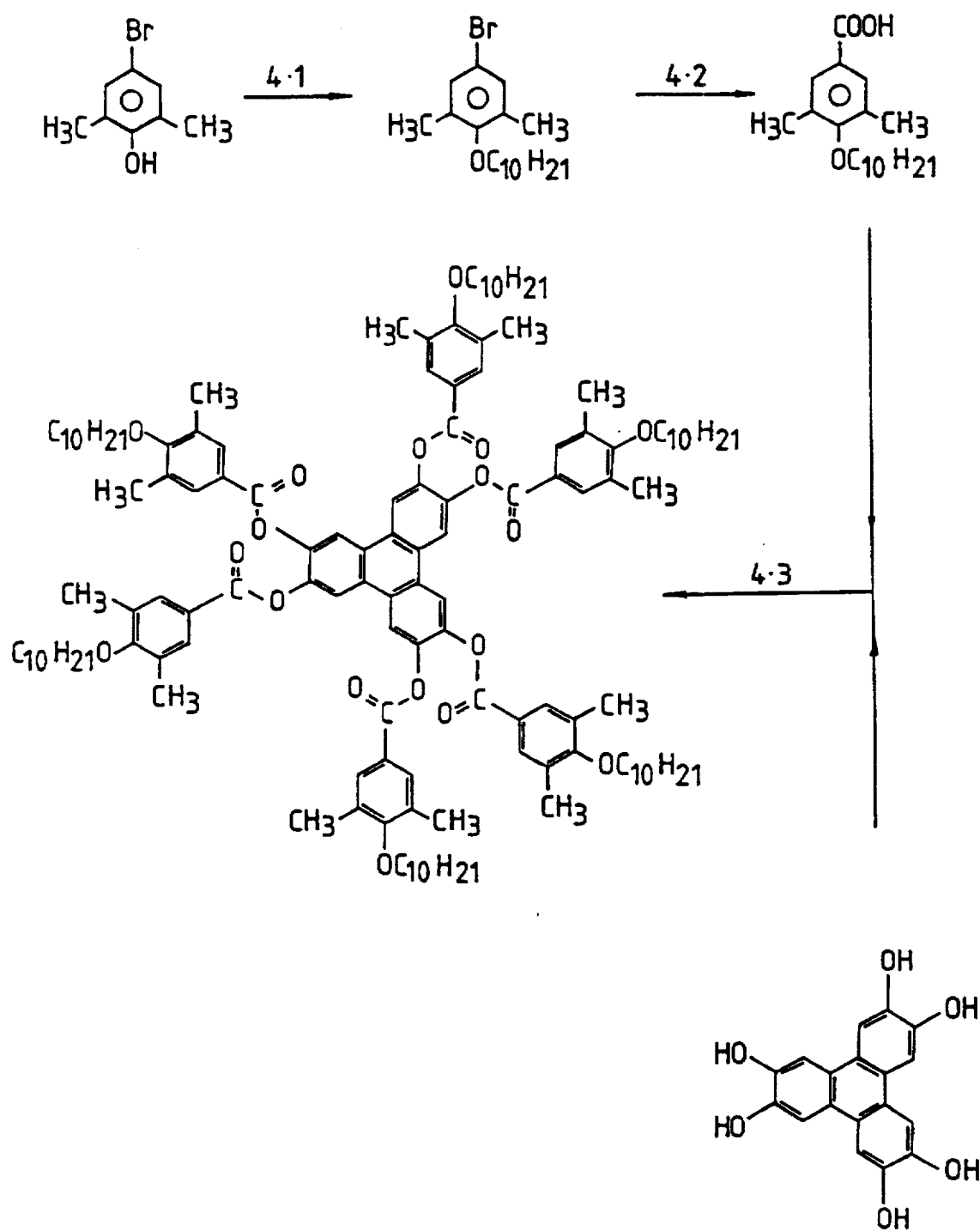
FIG. 4 is a synthetic route for preparing the compound of Example 4.
Figure 5:
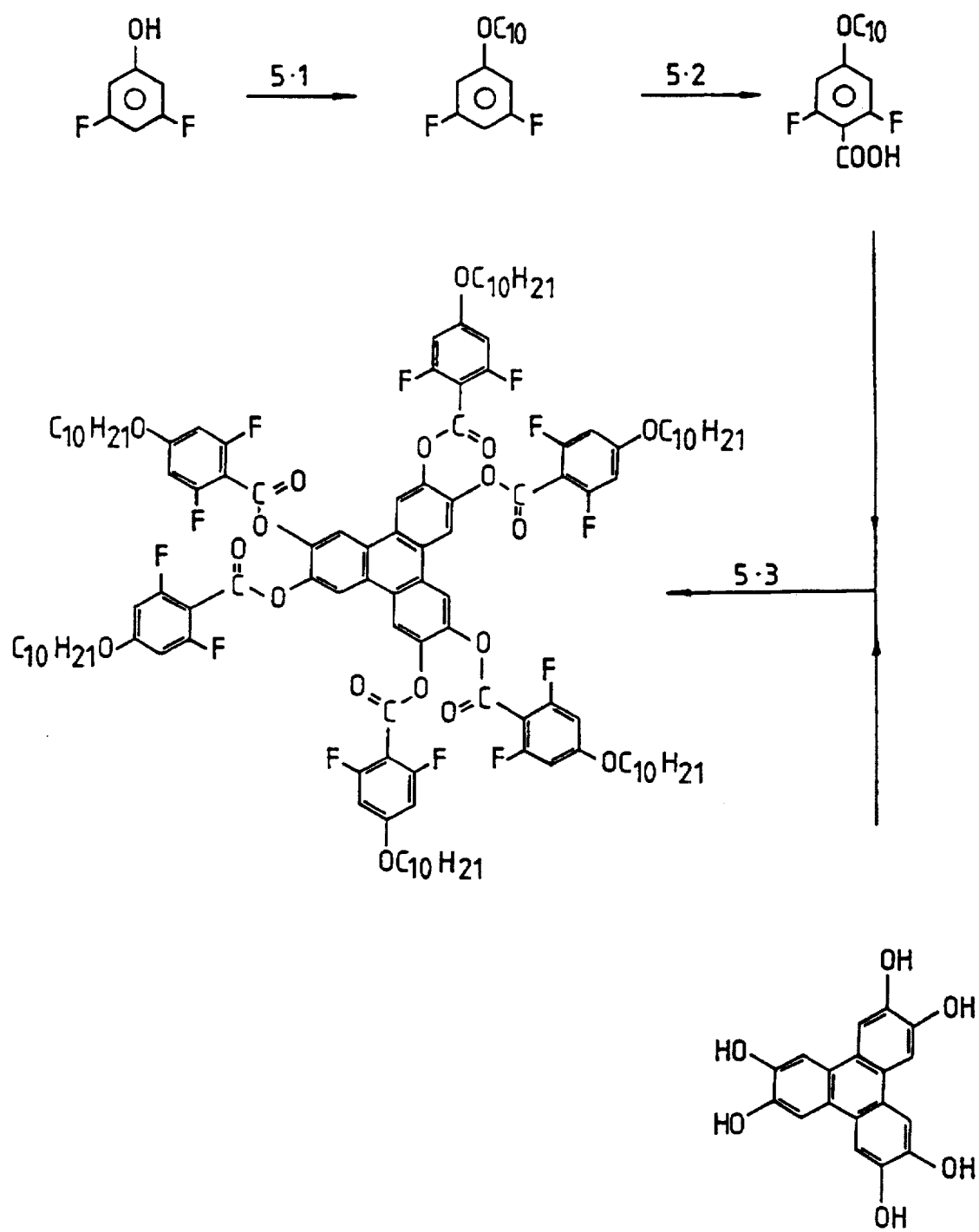
FIG. 5 is a synthetic route for preparing the compound of Example 5.
Figure 6:
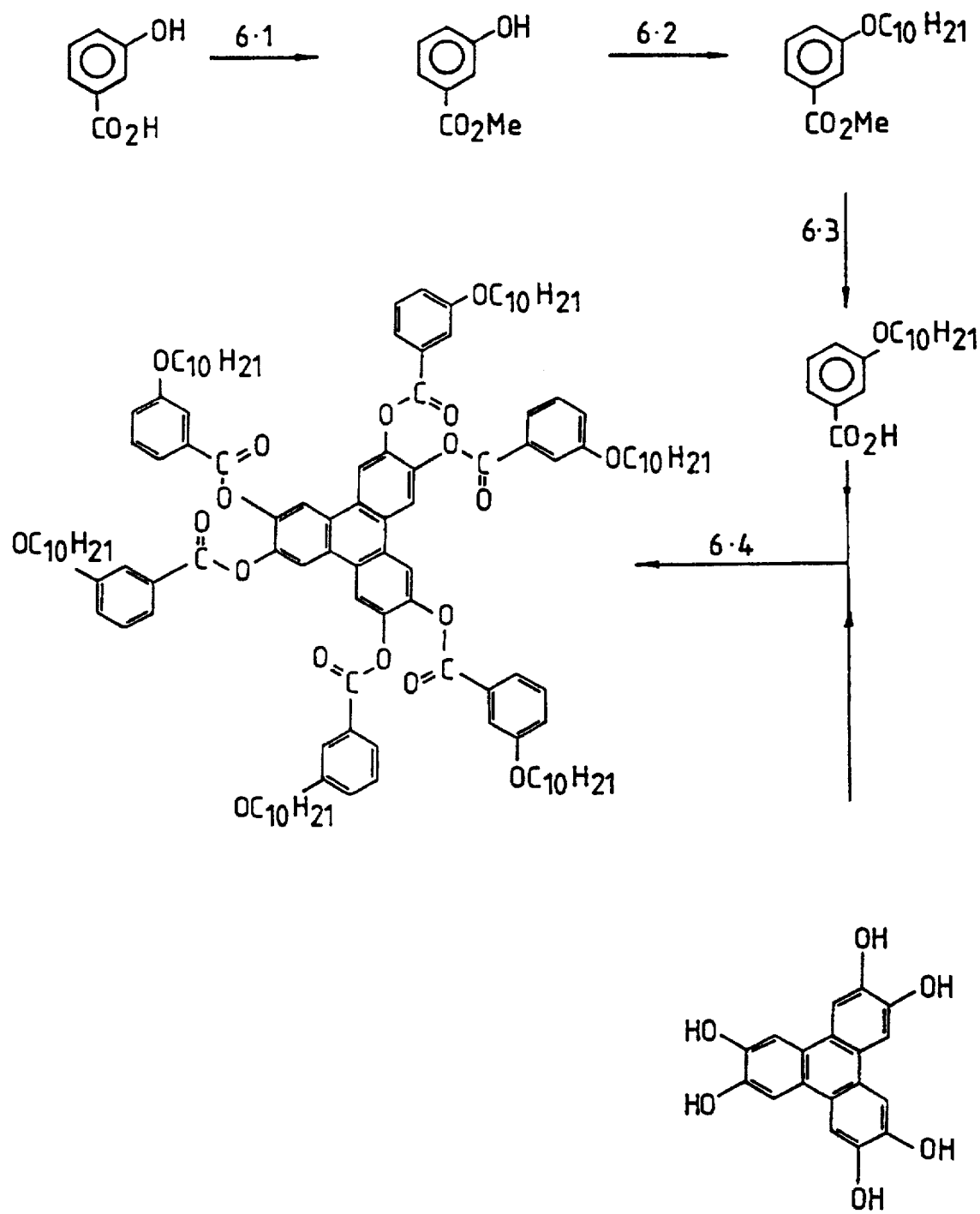
FIG. 6 is a synthetic route for preparing the compound of Example 6.
Figure 7:
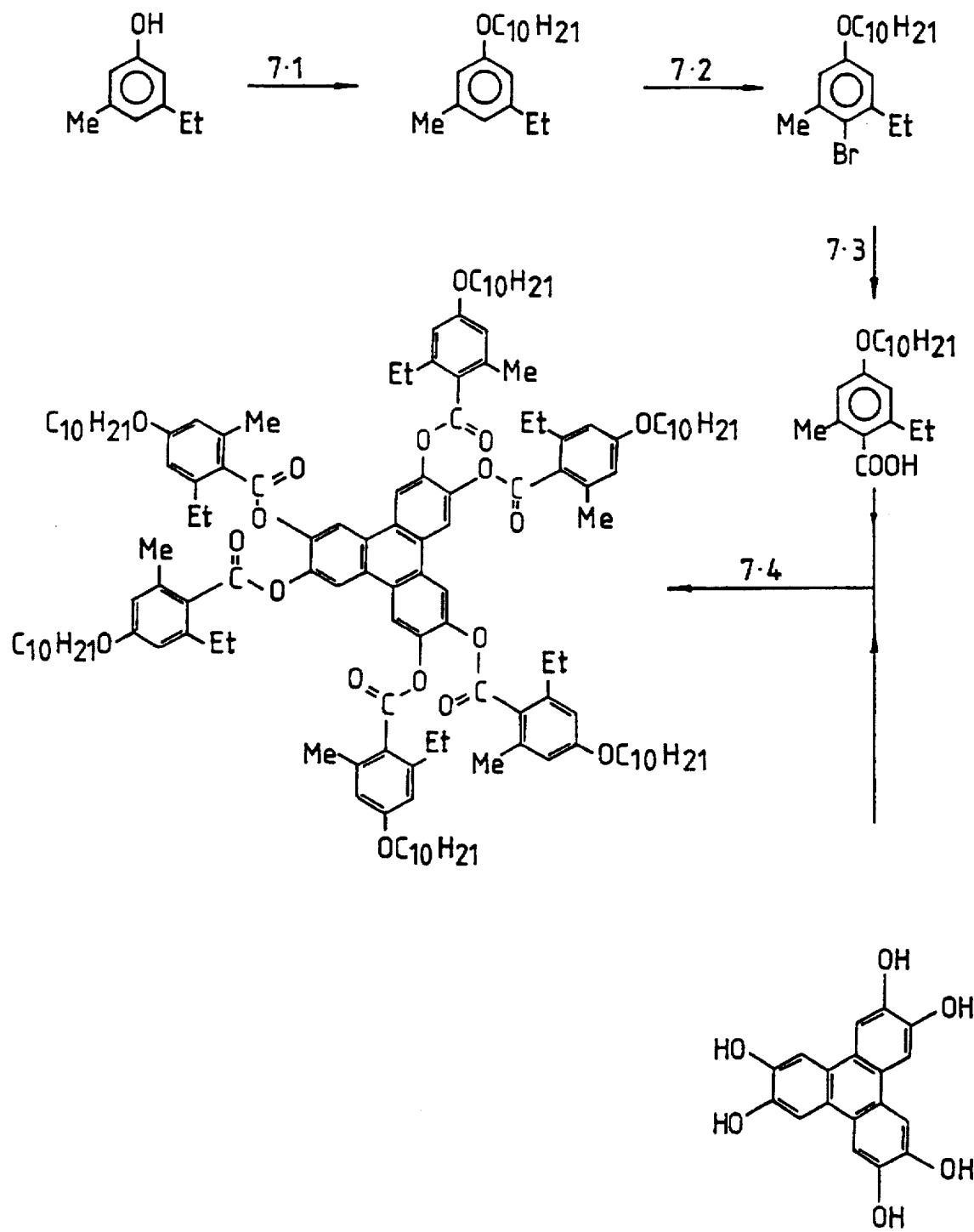
FIG. 7 is a synthetic route for preparing the compound of Example 7.

According to this invention 2,3,6,7,10,11 triphenylene discotic compounds are provided of Formula I:

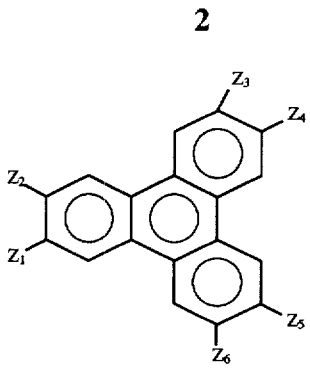

Formula I where each of $Z_{1-6}$ is given by Formula II:

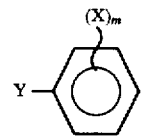

Formula II where Y for each of $Z_{1-6}$ is independently selected from COO, OCO, $CH_2O$, and $OCH_2$, m defines the number of substituents on each of $Z_{1-6}$ and is independently selected from 0–5, and X is independently selected for each substituent on each of $Z_{1-6}$ from alkyl (straight chain, branched and chiral), alkoxy (straight chain, branched or chiral), alkanoyl (straight chain, branched or chiral), alkenyl (straight chain, branched or chiral), halogen, halogenoalkyl (straight chain, branched or chiral) and CN, provided that at least one of $Z_{1-6}$ has at least one substituent X, and excluding where m is 1 for each of $Z_{1-6}$, Y is COO for each of $Z_{1-6}$ and X is n-alkyl or n-alkoxy positioned para to Y for each of $Z_{1-6}$, and also where m is 5 for each of $Z_{1-6}$, Y is COO for each of $Z_{1-6}$ and for each $Z_{1-6}$ X is selected as n-alkoxy positioned para to Y and fluorine for all other substituents.

Where substituent(s) are selected from alkyl, alkoxy, or alkenyl, then such substituents are preferably selected from $C_{1-20}$.

The structural preferences discussed below are inter alia on the basis of ease of preparation and/or usefulness in liquid crystal materials.

Preferred structures for each of independently selected $Z_{1-6}$ are given below:

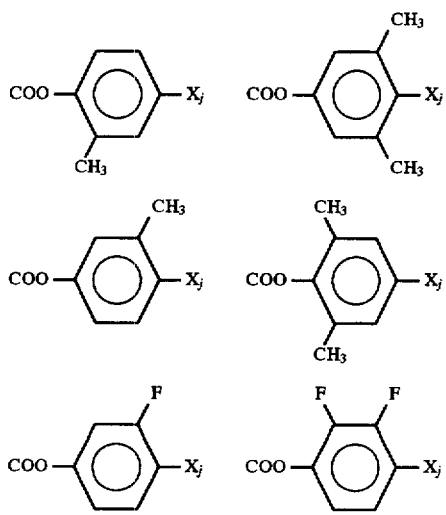

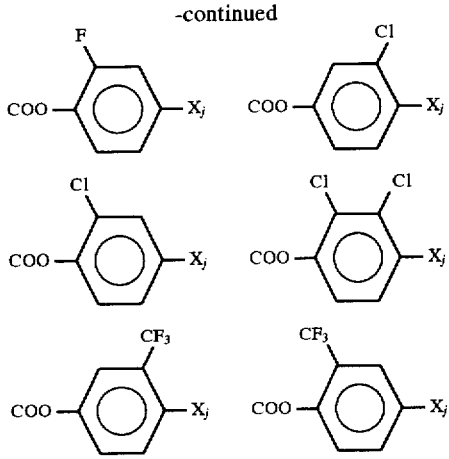

where $X_j$ is selected from alkyl, alkoxy, halogen (preferably fluorine) and CN.

Typically compounds of Formula I can be prepared by reaction of the appropriately substituted benzoic acid with the appropriate triphenylene biphenol. Preparation of triphenylene phenols is known (eg N H Tinh et al Mol. Cryst. Liq. Cryst., (1981), Vol 68, pp 101–111). The appropriately substituted benzoic acid can be prepared from synthetic routes apparent to persons skilled in the art.

In another aspect of this invention, compound(s) of Formula I can be included in a mixture, where the mixture comprises at least two compounds. Typical mixtures include mixtures consisting of compounds of Formula I, and also mixtures comprising at least one compound of Formula I and at least one compound not of Formula I. Donor/acceptor mixtures, and mixtures having lower melting points than melting points of individual compounds, are desirable for obtaining room temperature liquid crystal phases in discotic liquid crystal materials and for control of phase sequence and transition temperatures.

A further aspect of the invention includes use of the compounds of Formula I, and use of mixtures including Formula I, in a liquid crystal device. Typically such devices include linear and non-linear electrical, optical and electro-optical devices, magneto-optical devices, and devices providing responses to stimuli such as temperature changes and total or partial pressure changes.

DESCRIPTION OF THE PREFERRED EMBODIMENTS

The invention will now be described by way of example only, in which FIGS. 1–7 describe synthetic routes for the preparation of example compounds 1–7. FIGS. 8–12 are phase diagrams illustrating wt % of compound versus temperature. FIG. 13 illustrates a liquid crystal device.

Compound 1. Preparation of Triphenylen-2,3,6,7,10,11-yl hexa-4-octyloxy-3-methylbenzoate.

Step 1.1 Preparation of hexamethoxytriphenylene.

Chloranil (64 g, 0.26 mol), veratrol (14.4 g, 0.104 mol) and dilute sulphuric acid (70% v/v, 200 ml) were added together under nitrogen with stirring. The reaction was left for 8 days. The contents of the flask were poured onto ice (1 liter) and further diluted in 3 liters of water. The solid was filtered off. The product was first resuspended in 1 liter of water and 100 ml methanol and filtered off. This procedure was repeated using 500 ml methanol and 50 ml of water and finally with 1 liter of methanol. The product was then filtered off and dried. The material was then taken up into chloroform and filtered, this procedure was repeated several times. The combined chloroform extracts were evaporated and the solid stirred with 3×100 ml of toluene, filtered off and air dried. Then the solid was stirred with 3×100 ml of acetone, filtered off and air dried. The crude product was suspended in 100 ml chloroform together with 20 g of silica (Merck 60H, ART 7736). This slurry was added to a column of silica (60H, 80 g) in a 1 liter cylindrical separating funnel and eluted with chloroform. The fractions collected were stirred with an equal volume of toluene +3×that volume of methanol. The precipitated hexamethoxytriphenylene was then filtered off.

Yield: 3.26 g, (23%).

Melting point: 315° C.

Step 1.2 Preparation of hexahydroxytriphenylene.

Boron tribromide (8.6 g, 0.034 mol) in dry dichloromethane (80 ml) was added to hexamethoxytriphenylene (2 g, 0.0049 mol) in dry dichloromethane (100 ml) under a dry nitrogen atmosphere at −80° C. The mixture was allowed to warm to room temperature overnight. Water was added and the dichloromethane was removed under reduced pressure. The crude product was filtered off. The hexahydroxytriphenylene was purified by recrystallisation from water.

Yield: 1 g. (63%).

Melting Point: >310° C.

Step 1.3 Preparation of 2-methylphenyl acetate.

Ice (300 g) was added to o-cresol (21.6 g, 0.2 mol) dissolved in a solution of sodium hydroxide (12 g, 0.3 mol in water (100 ml). Acetic anhydride (30.6 g, 0.3 mol) was then added and the mixture was shaken for 1 min. The product was extracted into ether and then purified by reduced pressure distillation.

Yield: 25 g, (83.3%).

Boiling point: 66° C., 1 mmHg.

Step 1.4 Preparation of 4-hydroxy-3-methylacetophenone.

Compound of step 1.3 (24.7 g, 0.16 mol) in dry nitrobenzene (125 ml) was added dropwise with stirring to a suspension of anhydrous aluminium chloride (42.6 g, 0.32 mol) in dry nitrobenzene (250 ml) cooled in ice. The mixture was allowed to warm to room temperature and the stirring was continued for 10 hrs. The mixture was then poured onto ice and concentrated hydrochloric acid (100 ml) and stirred for 0.5 hrs. The organic layer was separated, and the aqueous layer was shaken with chloroform. The combined organic layers were washed with brine and then steam distilled until no further solvent (chloroform and nitrobenzene) passed over. The resultant crude product was extracted into chloroform and dried over anhydrous magnesium sulphate. After the chloroform was removed, the methyl-ketone was purified by recrystallisation from a 1:1 mixture of ethyl acetate and petroleum fraction (b.p. 60°–80° C.).

Yield: 5.36 g, (22%).

Melting point: 107°–109° C.

Step 1.5 Preparation of 3-methyl-4-octyloxyacetophenone.

Compound of step 1.4 (5 g, 0.033 mol) was added with stirring to a suspension of potassium carbonate (22.77 g, 0.165 mol) in butanone (110 ml). Bromo-octane (6.76 g, 0.035 mol) was then added dropwise. The mixture was stirred under reflux for 24 hrs. The solid was filtered off and half of the solvent was removed. The solution was then poured into water and the product was extracted into ethyl acetate. The combined extracts were washed with aqueous sodium hydroxide (5%) and then with water. After drying the extract over anhydrous magnesium sulphate. The methyl-ketone was purified by reduced pressure distillation.

Yield: 5.58 g. (64%).

Boiling point: 174° C., 1 mmHg.

Step 1.6 Preparation of 3-methyl-4-octyloxybenzoic acid.

A solution of sodium hypobromite was prepared at −10°–0° C. by dissolving bromine (12.8 g, 0.08 mol) in a solution of sodium hydroxide (8 g, 0.2 mol) in water (38 ml). This solution was added with stirring to a solution of compound of step 1.5 (3 g, 0.0115 mol) in dioxan (125 ml). The temperature was maintained at 60°–70° C. throughout the addition and for a further 20 mins. The excess of hypobromite was destroyed with sodium metabisulphite. Water was added to the reaction mixture, the white precipitate was filtered off and then the solution was acidified with concentrated hydrochloric acid. The precipitate was filtered off, washed several times with water, and then dried over anhydrous magnesium sulphate. The acid was purified by recrystallisation from ethanol.

Yield: 1.42 g, (46%).

Transitions (°C.): $K_1$ 70.9 $K_2$ 112.4 (N 102.4) IL.

Step 1.7 Preparation of Triphenylen-2,3,6,7,10,11-yl hexa-4-octyloxy-3-methylbenzoate.

Compound of step 1.6 (10 g, 0.038 mol) and Dimethylformamide (5 drops) were dissolved in dry dichloromethane (100 ml) and oxalyl chloride (9.6 g, 0.076 mol) in dry dichloromethane (10 ml) was added dropwise. The mixture was stirred at room temperature overnight. The excess of oxalyl chloride and dichloromethane was removed in vacuo (60° C.) and the residual acid chloride was then used at once to prepare the ester. 3-methyl-4-octyloxybenzoyl chloride (0.038 mol) was added to the compound of step 1.2 (0.6 g, 0.0019 mol) in anhydrous pyridine (100 ml). The mixture was heated with stirring at 160° C. for 2 hrs and then poured onto a mixture of concentrated hydrochloric acid (50 ml) and crushed ice (500 ml). The crude product was extracted into ether, washed with water, and dried over anhydrous magnesium sulphate. The solvent was removed and the product was purified by flash column chromatography (dichloromethane eluent) and successive recrystallisations from ethanol.

Yield: 0.8 g, (23%).

Transitions (°C.): K 50 $N_D$ 208 IL.

Compound 2. Preparation of Triphenylen-2,3,6,7,10,11-yl hexa-4-decyloxy-3-fluorobenzoate.

Step 2.1 Preparation of 4-Bromo-1-decyloxy-2-fluorobenzene.

A solution of 1-bromodecane in butanone was added dropwise to a stirred refluxing solution of 4-bromo-2-fluorophenol and potasium carbonate. The stirred mixture was heated under reflux for 24 hr. The potassium carbonate was filtered off and the solvent removed. The product was distilled at 130° C. at 0.05 mmHg.

Step 2.2 Preparation of 4-decyloxy-3-fluorobenzoic acid.

A solution of n-butyllithium was added dropwise to a stirred, cooled (−78° C.) solution of compound of step 2.1 in dry THF. The mixture was maintained under these conditions for 40 mins and then poured into a slurry of dry ether and cardice. The solution was acidified with 36% HCl, washed with water and dried (magnesium sulphate). The solvent was removed to yield a white solid.

K 103.5 $S_c$ 109.6N 114.7 I

Step 2.3 Preparation of Triphenylen-2,3,6,7,10,11-yl hexa-4-decyloxy-3-fluorobenzoate.

Compound of step 2.2 and dimethylformamide were dissolved in dry dichloromethane. A solution of oxalyl chloride in dry dichloromethane was added dropwise. The reaction was left overnight and then solvent and excess oxalyl chloride was removed. The residual acid chloride was used immediately. Compound of step 1.2 was added to the acid chloride in dry pyridine at 160° C. and heated under reflux for 2 hours. The reaction was cooled and poured into a mixture of 36% HCl/ice. The crude product was extracted into ether, washed with water, sodium bicarbonate, water and dried (magnesium sulphate). The solvent was removed to yield a crude product, which was recrystallised in benzene.

K 175 $M_1$ 216 $M_2$ about 320 $M_3$ about 430 I (decomposes) where $M_{1-3}$ are considered to be unknown mesophases.

Compound 3. Preparation of Triphenylen-2,3,6,7,10,11-yl hexa-4-decyloxy-2,6-dimethyl benzoate.

Step 3.1. Preparation of 1-Bromo-4-decyloxy-2,6-dimethylbenzene.

The experimental procedure was as described for the preparation of the compound formed by step 2.1

A solution of 1-bromodecane (11.05 g, 0.05 mol) in butanone (50 ml) was added dropwise to a stirred, refluxing mixture of 4-Bromo-3,5-dimethylphenol (8.0 g, 0.04 mol) and anhydrous potassium carbonate $K_2CO_3$ (30.0 g, 0.2 mol) in butanone (250 ml). The stirred mixture was heated under reflux for 24 h. The $K_2CO_3$ was filtered off and the solvent removed. The residue was distilled to yield a colourless liquid.

Step 3.2. Preparation of 4-Decyloxy-2,6-dimethylbenzoic acid

The experimental procedure was as described for the preparation of the compound formed by step 2.2

A solution of n-butyllithium (2.9 ml, 10.0M in hexane, 0.029 mol) was added dropwise to a stirred, cooled (−78° C.) solution of 1-Bromo-4-decyloxy-2,6-dimethylbenzene (10.0 g, 0.029 mol) in dry THF (200 ml) under dry nitrogen. The stirred mixture was maintained under these conditions for 1 h and then poured onto a slurry of solid carbon dioxide and dry ether. The product was acidified with 36% HCl and washed with water. The ether layer was dried ($MgSO_4$) and the solvent removed to give a colourless solid which was recrystallised from petroleum fraction (40°–60° C.).

Yield: 2.64 g (30%)

mp=80°–81° C.

Step 3.3 Preparation of Triphenylen-2,3,6,7,10,11-yl hexa-4-decyloxy-2,6-dimethyl benzoate.

A solution of oxalyl chloride (1.26 g, 0.01 mol) in dry dichloromethane was added dropwise to a stirred solution of 4-Decyloxy-2,6-dimethylbenzoic acid (2.44 g, 0.008 mol) and DMF (10 drops) in dry dichloromethane (100 ml). The reaction was left overnight and then the solvent was removed. The residual acid chloride was used immediately without further purification.

2,3,6,7,10,11-Hexahydroxytriphenylene (0.26 g, 0.0085 mol) was added all at once to the acid chloride in dry pyridine and was heated under reflux (oilbath temperature at >160° C.) for 2 h. The reaction mixture was cooled and poured into a mixture of concentrated hydrochloric acid and ice. The crude product was extracted into ether, washed with water, aqueous $NaHCO_3$, water and dried ($MgSO_4$). The solvent was removed, the crude product was purified by flash column chromatography and recrystallised from ethanol/ethyl acetate.

Yield: 2.68 g (58%)

Compound 4: Preparation of Triphenylen-2,3,6,7,10,11-yl hexa-4-decyloxy-3,5-dimethyl benzoate.

Step 4.1 Preparation of 1-Bromo-4-decyloxy-3,5-dimethylbenzene.

The experimental procedure was as described for the preparation of 1-Bromo-4-decyloxy-2,6-dimethylbenzene (see step 3.1) and the product was distilled.

Quantities: 4-Bromo-2,6-dimethylphenol (8.0 g, 0.04 mol), 1-bromodecane (11.05 g, 0.05 mol), $K_2CO_3$ (30.0 g, 0.2 mol).

Yield: 12.0 g, (88%).

bp=150°–160° C. at 0.01 mm Hg.

Step 4.2. Preparation of 4-Decyloxy-3,5-dimethylbenzoic acid

The experimental procedure was as described for the preparation of 4-Decyloxy-2,6-dimethylbenzoic acid (see step 3.2). The product was recrystallised from petroleum fraction (40°–60° C.).

Quantities: 1-Bromo-4-decyloxy-3,5-dimethylbenzene (12.0 g, 0.039 mol), n-butyllithium (3.9 ml, 10.0M in hexane, 0.039 mol).

Yield: 4.44 g, (37%)

mp=77°–78° C.

Step 4.3: Preparation of Triphenylen-2,3,6,7,10,11-yl hexa-4-decyloxy-3,5-dimethyl benzoate.

The experimental procedure was as described for the preparation of Triphenylen-2,3,6,7,10,11-yl hexa-4-decyloxy-2,6-dimethyl benzoate (see step 3.3).

Quantities: 1-Bromo-4-decyloxy-3,5-dimethylbenzene (4.0 g, 0.013 mol), oxalyl chloride (3.78 g, 0.03 mol), 2,3,6,7,10,11-Hexahydroxytriphenylene (0.42 g, 0.0013 mol).

Yield: 0.28 g (11%)

Compound 5: Preparation of Triphenylen-2,3,6,7,10,11-yl hexa-4-decyloxy-2,6-difluorobenzoate.

This compound was synthesised in a similar manner as that described for compound 2.

Step 5.1 Preparation of 1-Decyloxy-3,5-difluorobenzene.

The experimental procedure was as described for the preparation of 1-Bromo-4-decyloxy-3-fluorobenzene (see step 2.1).

Quantities: 3,5-difluorophenol (5.0 g, 0.038 mol), 1-bromodecane (8.84 g, 0.04 mol).

Yield: 10.26 g (100%)

Step 5.2 Preparation of 4-Decyloxy-2,6-difluorobenzoic acid

The experimental procedure was as described for the preparation of 4-decyloxy-3-fluorobenzoic acid (see step 2.2).

Quantities: 1-Decyloxy-3,5-difluorobenzene (10.26 g, 0.038 mol), n-BuLi (10.0M), (3.8 ml, 0.038 mol), THF (200 ml).

Yield: 7.7 g, (64%).

Step 5.3 Preparation of Triphenylen-2,3,6,7,10,11-yl hexa-4-decyloxy-2,6-difluorobenzoate.

The experimental procedure was as described for the preparation of triphenylen-2,3,6,7,10,11-yl hexa-4-decyloxy-3-fluorobenzoate (see step 2.3).

Quantities: 4-Decyloxy-2,6-difluorobenzoic acid (7.7 g, 0.024 mol), oxalyl chloride (3.78 g, 0.03 mol), DMF (10 drops), dichloromethane (100 ml), hexahydroxytriphenylene (0.77 g, 0.0024 mol), pyridine (100 ml).

Yield: 3.00 g (60%)

Phase Transition/°C.: K 138.0 I

Compound 6: Preparation of Triphenylen-2,3,6,7,10,11-yl hexa-3-decyloxybenzoate.

This compound was synthesised in a similar manner as that described for compound 2.

Step 6.1 Preparation of Methyl 3-hydroxybenzoate.

3-hydroxybenzoic acid (30.0 g, 0.22 mol), methanol (101 ml) and concentrated sulphuric acid (2.7 ml) were added together and heated under reflux for 4 h. The reaction mixture was allowed to cool and the methanol was removed. The crude product was dried in vacuo and used without further purification.

Yield: 32.98 g, (100%).

Step 6.2 Preparation of Methyl 3-decyloxybenzoate.

A solution of 1-bromodecane (11.05 g, 0.050 mol) in butanone (50 ml) was added dropwise to a stirred, refluxing mixture of methyl-3-hydroxybenzoate (5.0 g, 0.033 mol) and anhydrous potassium carbonate ($K_2CO_3$) (30.0 g, 0.20 mol) in butanone (200 ml). The stirred mixture was heated under reflux for 24 h. The $K_2CO_3$ was filtered off and the solvent removed. The residue was purified by gravity column chromatography (silica gel/dichloromethane) to yield a colourless oil.

Yield: 9.64 g, (100%).

Step 6.3 Preparation of 3-Decyloxybenzoic acid.

A solution of methyl 3-decyloxybenzoate (9.64 g, 0.033 mol) and sodium hydroxide (6.60 g, 0.165 mol) in methanol (150 ml) and water (15 ml) was heated under reflux for 2 h. The reaction mixture was then allowed to cool, followed by addition of dilute HCl (100 ml). The crude product was filtered off, washed with water and then dried in vacuo. The material was recrystallised to yield colourless crystals.

Yield: 7.60 g, (82%).

Step 6.4 Preparation of Triphenylen-2,3,6,7,10,11-yl hexa-3-decyloxybenzoate.

The method of preparation of this compound was the same as for step 3.3

Yield: 4.83 g (95%)

Phase Transition/°C.: K 134.0 I

Compound 7: Preparation of Triphenylen-2,3,6,7,10,11-yl hexa-4-decyloxy-2-ethyl-6-methylbenzoate.

Step 7.1 Preparation of 1-Decyloxy-3-ethyl-5-methylbenzene.

The experimental procedure was as described for 1-Bromo-4-decyloxy-3-fluorobenzene (see step 2.1) to yield a pale orange oil.

Quantities: 3-ethyl-5-methylphenol (5.0 g, 0.036 mol), 1-bromodecane (11.05 g, 0.05 mol), $K_2CO_3$ (30.0 g, 0.2 mol).

Yield: 9.4 g (94%).

Step 7.2 Preparation of 1-Bromo-4-decyloxy-2-ethyl-6-methylbenzene

A solution of bromine (5.44 g, 0.034 mol) in chloroform (50 ml) was added dropwise to a stirred, refluxing solution of 1-decyloxy-3-ethyl-5-methylbenzene (9.4 g, 0.034 mol) in chloroform (200 ml). The reaction mixture was then allowed to cool, washed with water and dried ($MgSO_4$). The solvent was removed and the residue purified by gravity column chromatography (silica gel/dichloromethane) to yield a pale orange oil.

Yield: 11.57 g (96%).

Step 7.3 Preparation of 4-Decyloxy-2-ethyl-6-methylbenzoic acid

The experimental procedure was as described for the preparation of the compound synthesised in step 2.2. The crude product was recrystallised from petroleum fraction (40°–60° C.) to yield a colourless solid.

Quantities: 1-bromo-4-decyloxy-2-ethyl-6-methylbenzene (11.57 g, 0.036 mol), n-BuLi (3.6 ml, 10.0M, 0.036 mol), THF (200 ml).

Yield: 4.32 g (48%).

Step 7.4 Preparation of Triphenylen-2,3,6,7,10,11-yl hexa-4-decyloxy-2-ethyl-6-methylbenzoate.

The experimental procedure was as described for compound 2, (see step 2.3).

Quantities: 4-decyloxy-2-ethyl-6-methylbenzoic acid (4.32 g, 0.0135 mol), oxalyl chloride (1.89 g, 0.015 mol), DMF (10 drops), dichloromethane (100 ml), hexahydroxytriphenylene (0.44 g, 0.00135 mol), pyridine (100 ml).

Yield: 1.15 g (40%).

Phase Transition: K–$N_D$ 70.0 I

Tables 1 and 2 give phase transition temperatures for compounds of Formula I, where Formula III describes each of $Z_{1-6}$ for Table 1, Formula IV describes each of $Z_{1-6}$ for Table 2, and K is crystalline, D is a columnar phase, $N_D$ is nematic discotic phase and IL is isotropic liquid. Formula V describes each of $Z_{1-6}$ for Table 3, Formula VI describes each of $Z_{1-6}$ for Table 4. K is crystalline. D is a columnar phase, $N_D$ is nematic discotic phase, hd is hexagonal disordered and IL is isotropic liquid.

Formula III
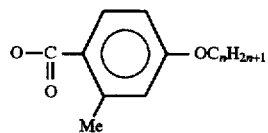

Formula IV
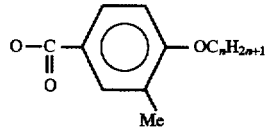

Formula V
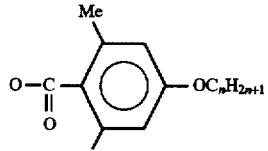

Formula VI
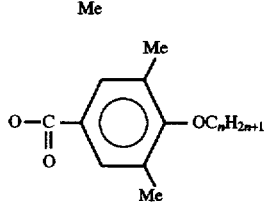

All phase transition temperatures were obtained by microscopy, unless described within brackets. Data within brackets indicates that phase transition temperatures were obtained using a differential scanning calorimeter.

TABLE 1

| n | Phase Transition Temperatures (°C.) |
|---|---|
| 6 | K 185 $N_D$ 242 IL |
|   | (K 59 D 110 $N_D$ 242 IL) |
| 7 | K 152 $N_D$ 215 IL |
|   | (K 30 D 138 $N_D$ 209 IL) |
| 8 | K 50 $N_D$ 208 IL |
|   | (K 37 D 123 $N_D$ 205 IL) |
| 9 | K 114 $N_D$ 202 IL |
|   | (K 40 D 113 $N_D$ 201 IL) |
| 10 | K 77 $N_D$ 180 IL |
|   | (K 40 D 94 $N_D$ 178 IL) |
| 11 | K 92 $N_D$ 165 IL |
|   | (K 92 $N_D$ 154 IL) |
| 12 | K 126 $N_D$ 166 IL |
|   | (K 44 D 90 $N_D$ 163 IL) |

TABLE 2

| n | Phase Transition Temperatures (°C.) |
|---|---|
| 7 | K 145 $N_D$ 208 IL |
|   | (K 32 D 139 $N_D$ 201 IL) |
| 8 | K 127 $N_D$ 199 IL |
|   | (K 67 D 123 $N_D$ 195 IL) |
| 9 | K 114 $N_D$ 179 IL |
|   | (K 45 D 108 $N_D$ 174 IL) |
| 10 | K 109 $N_D$ 180 IL |
|   | (K 40 $N_D$ 164 IL) |
| 11 | K 106 $N_D$ 136 IL |
|   | (K 103 $N_D$ 134 IL) |
| 12 | K 105 $N_D$ 115 IL |
|   | (K 97 $N_D$ 141 IL) |

TABLE 3

| | Phase Transitions/°C. | | |
|---|---|---|---|
| R | K | $N_D$ | I |
| $C_6H_{13}$ | * 170 | * 196 | * |
| $C_8H_{17}$ | * 155 | * 170 | * |
| $C_{10}H_{21}$ | * 108 | * 134 | * |
| $C_{12}H_{25}$ | * 88 | * 99 | * |
| $C_6H_{13}CH(CH_3)$ | * 161 | * — | * |

TABLE 4

| | Phase Transitions/°C. | | | |
|---|---|---|---|---|
| R | K | $D_{hd}$ | $N_D$ | I |
| $C_6H_{13}$ ¶ | * 150 | * 210 | * 243 | * |
| $C_8H_{17}$ | * 170 | * 195 | * 215 | * |
| $C_{10}H_{21}$ | * 157 | * 167 | * 182 | * |
| $C_{12}H_{25}$ | * | * 143 | * 151 | * |
| $C_6H_{13}CH(CH_3)$ | * 125 | * 156 | * 183 | * |

¶ DSC data; material decomposes under microscopic examination

Figure 8:
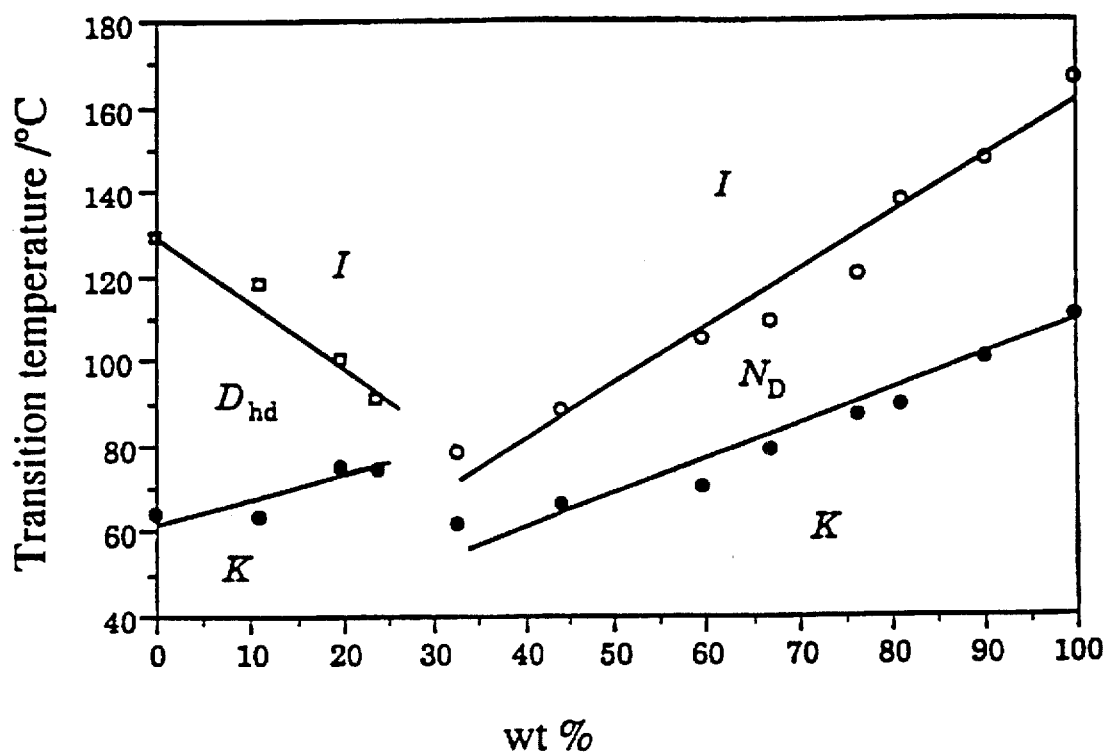
FIG. 8 is a phase diagram illustrating weight percent of a mixture of two compounds versus temperature.

The compounds of formula I may be added to other materials to form mixtures. FIG. 8 is a phase diagram showing the weight % of:

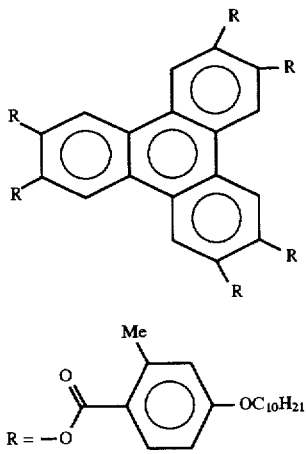

when mixed with the compound illustrated below versus transition temperature.

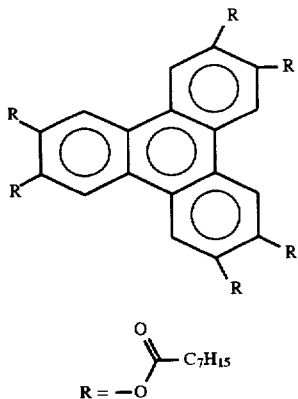

Figure 9:
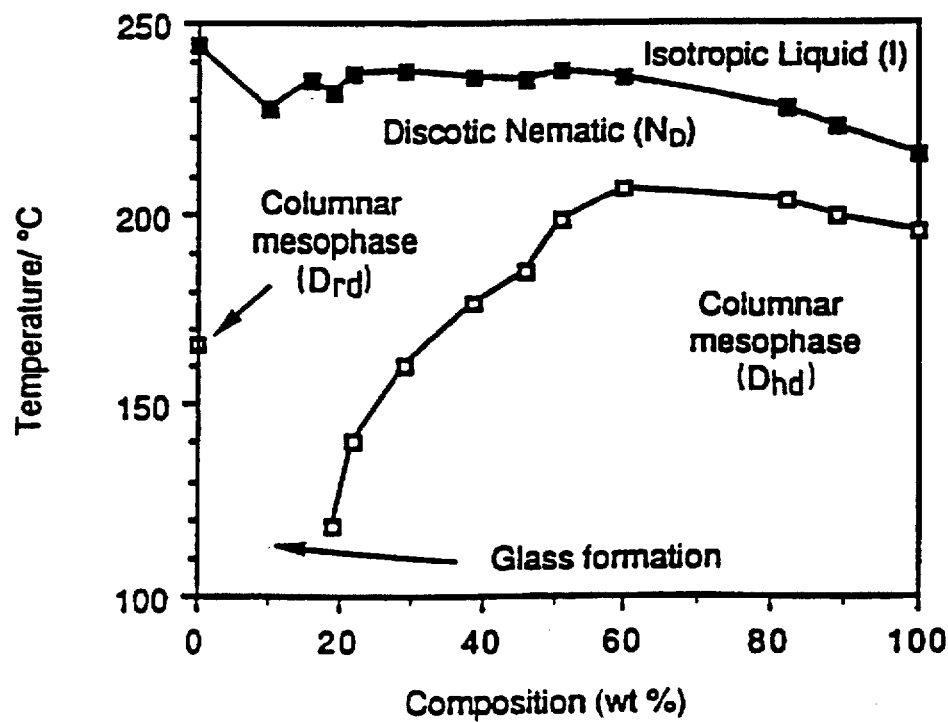
FIG. 9 is a phase diagram illustrating weight percent of compound versus temperature for selected compounds of pairs of compounds.

FIG. 9 is a binary phase diagram of transition temperatures plotted against % by weight for compounds triphenylen-2,3,6,7,10,11-yl hexa-4-octyloxybenzoate and triphenylen-2,3,6,7,10,11-yl hexa-4-octyloxy-3,5-dimethylbenzoate.

Figure 10:
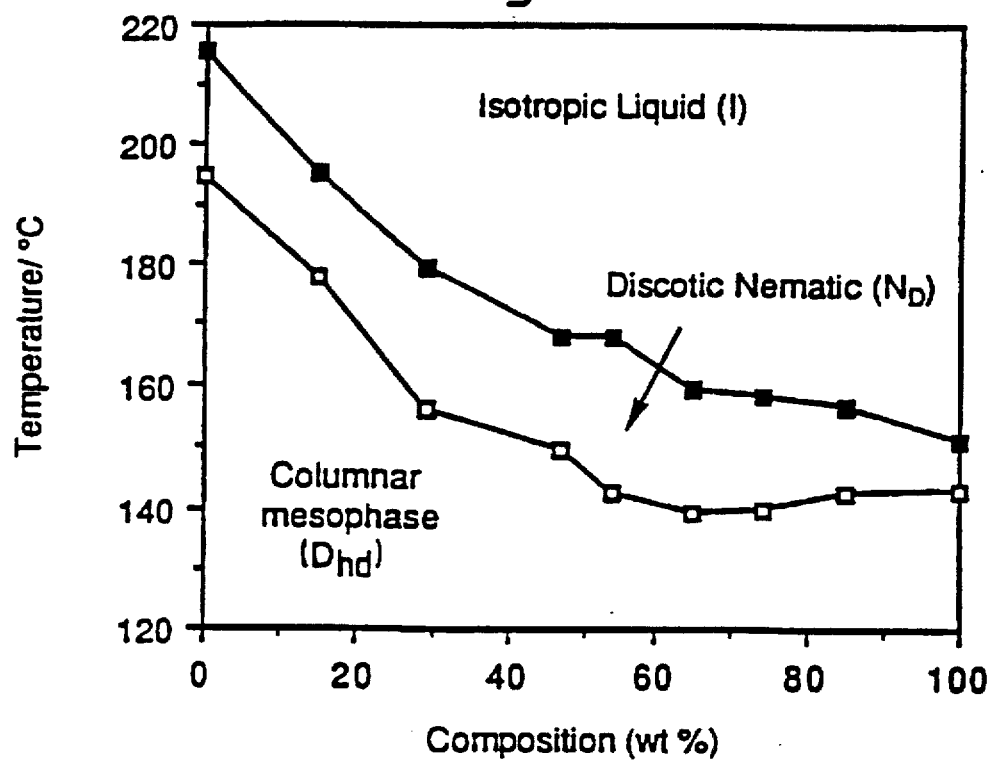
FIG. 10 is a phase diagram illustrating weight percent of compound versus temperature for selected compounds of pairs of compounds.

FIG. 10 is a binary phase diagram of transition temperatures plotted against % by weight for compounds triphenylen-2,3,6,7,10,11-yl hexa-4-octyloxy-3,5-dimethylbenzoate and triphenylen-2,3,6,7,10,11-yl hexa-4-dodecyloxy-3,5-dimethylbenzoate.

Figure 11:
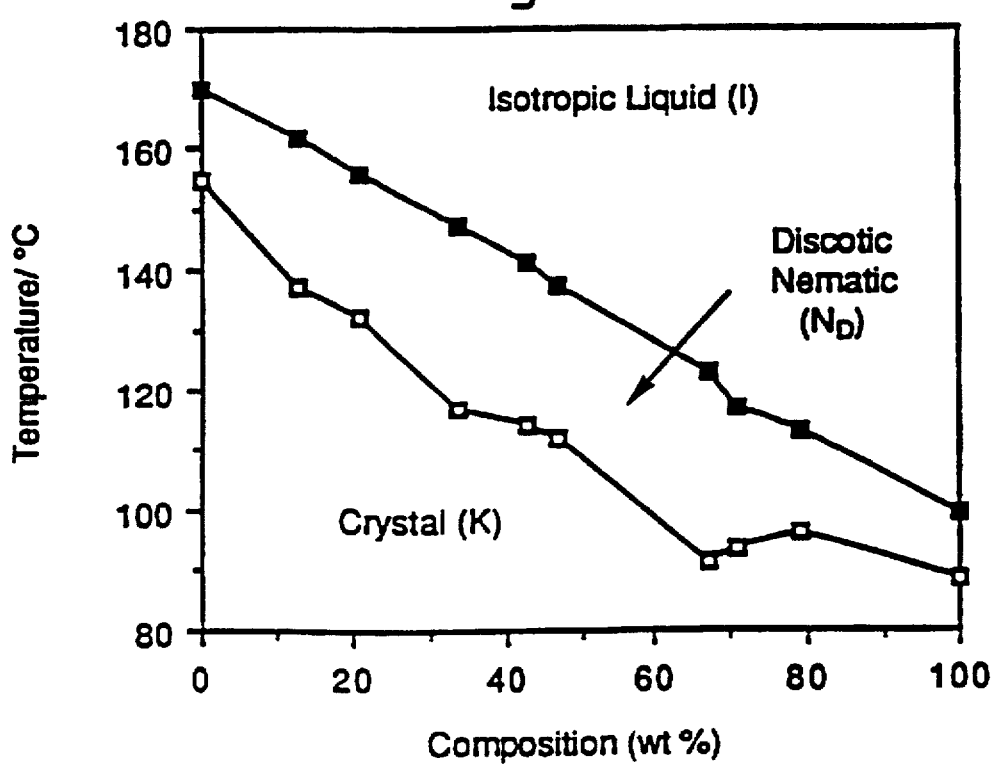
FIG. 11 is a phase diagram illustrating weight percent of compound versus temperature for selected compounds of pairs of compounds.

FIG. 11 is a binary phase diagram of transition temperatures plotted against % by weight for compounds triphenylen-2,3,6,7,10,11-yl hexa-4-octyloxy-2,6-dimethylbenzoate and triphenylen-2,3,6,7,10,11-yl hexa-4-dodecyloxy-2,6-dimethylbenzoate.

Figure 12:
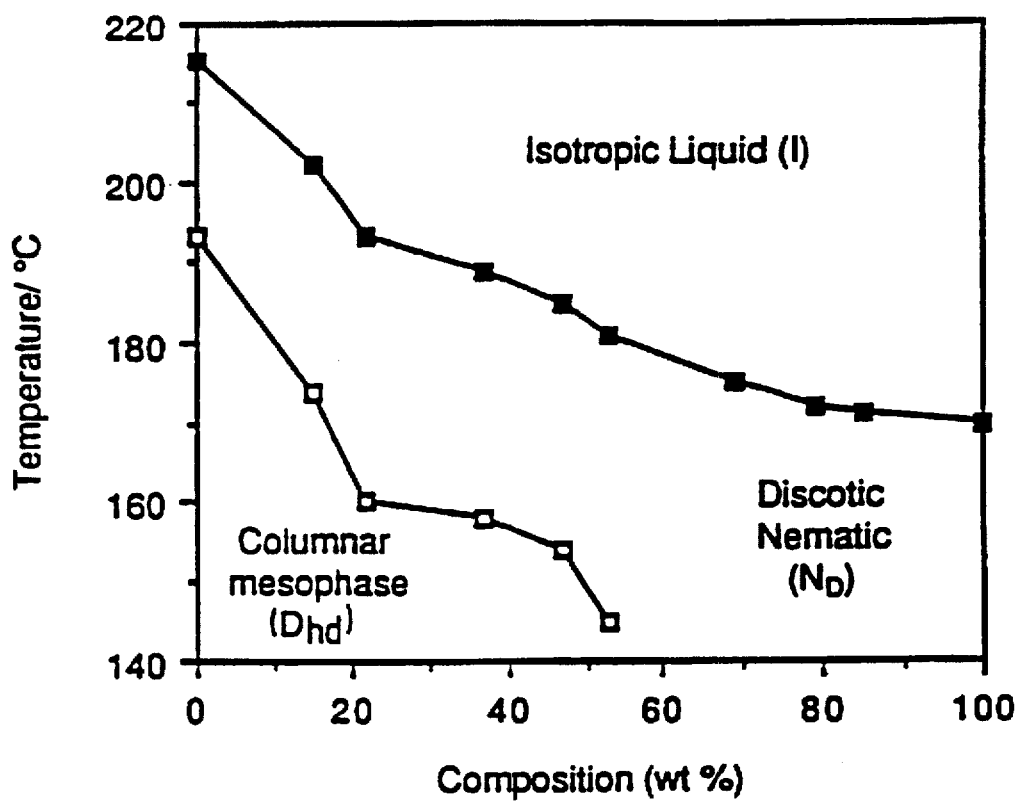
FIG. 12 is a phase diagram illustrating weight percent of compound versus temperature for selected compounds of pairs of compounds.
Figure 13:
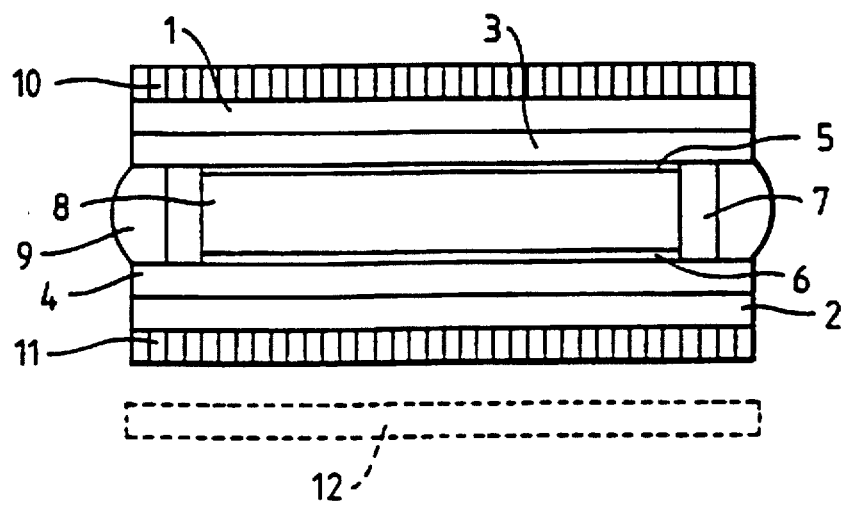
FIG. 13 is a schematic cross-section of a liquid crystal display device containing the liquid crystal materials of the present invention.

FIG. 12 is a binary phase diagram of transition temperatures plotted against % by weight for compounds triphenylen-2,3,6,7,10,11-yl hexa-4-octyloxy-3,5-dimethylbenzoate and triphenylen-2,3,6,7,10,11-yl hexa-4-octyloxy-2,6-dimethylbenzoate.

An example of the use of a compound of Formula I in a liquid crystal material and device embodying the present invention will now be described with reference to FIG. 13.

The liquid crystal device consists of two transparent plates, 1 and 2, in this case made from glass. These plates are coated on their internal face with transparent conducting electrodes 3 and 4. An alignment layer 5, 6 is introduced onto the internal faces of the cell so that a planar orientation of the molecules making up the liquid crystalline material will be approximately parallel or at a small angle to the glass plates 1 and 2. For some types of display the alignment directions are orthogonal. The electrodes 3, 4 may be formed into row and column electrodes so that the intersections between each column and row form an x, y matrix of addressable elements or pixels. A spacer 7 eg of polymethyl methacrylate separates the glass plates 1 and 2 to a suitable distance eg 2 microns.

Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell. For some devices, only one or even no polarisers are required.

The device may operate in a transmissive or reflective mode. In the former, light passing through the device, eg from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

In another example a layer of liquid crystal material is exposed to a gas to provide a gas sensor.

We claim:

1. A 2,3,6,7,10,11 triphenylene discotic compound of Formula I:

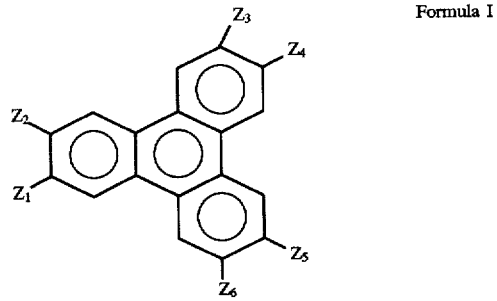

Formula I where each of $Z_{1-6}$ is given by Formula II:

Formula II where Y for each of $Z_{1-6}$ is independently selected from the group consisting of COO and OCO, m defines the number of substituents on each of $Z_{1-6}$ and is independently selected from the group consisting of 1–5, and X is independently on each of $Z_{1-6}$ selected from the group consisting of a straight chain, branched and chiral alkyl a straight chain, branched or chiral alkoxy, a straight chain, branched or chiral alkanoyl, a straight chain, branched or chiral alkenyl, halogen, a straight chain, branched or chiral halogenoalkyl and CN, provided that at least one of $Z_{1-6}$ has at least one substituent X which is in the ortho or meta position relative to the Y group excluding where m is 5 for each $Z_{1-6}$, Y is COO for each of $Z_{1-6}$ and for each $Z_{1-6}$ X is as n-alkoxy positioned para to Y and fluorine for all other substituents.

2. A triphenylene according to claim 1 wherein each of $Z_{1-6}$ is the same.

3. A triphenylene according to claim 1 where Y is COO for each of $Z_{1-6}$.

4. A triphenylene according to claim 3 where each $Z_{1-6}$ has a substituent positioned para with respect to Y, and the substituent for each of $Z_{1-6}$ is selected from the group consisting of alkyl, alkoxy, fluorine, chlorine and CN.

5. A triphenylene according to claim 4 where at least one $Z_{1-6}$ in the ortho or meta substituent portions is selected from the group consisting of $CH_3$, fluorine, chlorine and $CF_3$.

6. A triphenylene according to claim 4 where at least one $Z_{1-6}$ has three substituents, two of the substituents are selected from the group consisting of $CH_3$, fluorine, chlorine and $CF_3$, and are positioned ortho and meta with respect to Y.

7. A triphenylene according to claim 4 where at least one $Z_{1-6}$ has three substituents, two of the substituents are selected from the group consisting of $CH_3$, fluorine, chlorine and $CF_3$, and both are positioned meta with respect to Y.

8. A liquid crystal mixture, comprising at least two compounds, where at least one compound is a triphenylene according to claim 1.

9. A liquid crystal mixture, comprising at least two compounds, where all compounds in the mixture are triphenylenes according to claim 1.

10. A liquid crystal device incorporating a triphenylene according to claim 1.

* * * * *